United States Patent [19]
Gevirtz et al.

[11] Patent Number: 5,635,204
[45] Date of Patent: Jun. 3, 1997

[54] METHOD FOR TRANSDERMAL INDUCTION OF ANESTHESIA, ANALGESIA OR SEDATION

[75] Inventors: Clifford Gevirtz, New York; Hideo Nagashima, Bronx; David P. Katz, Dobbsferry, all of N.Y.

[73] Assignee: Montefiore Medical Center, Bronx, N.Y.

[21] Appl. No.: 205,939

[22] Filed: Mar. 4, 1994

[51] Int. Cl.⁶ .................................................. A61F 13/00
[52] U.S. Cl. ........................ 424/449; 424/447; 424/448
[58] Field of Search ................................. 424/447–449

[56] References Cited

U.S. PATENT DOCUMENTS

| | | | |
|---|---|---|---|
| 4,060,084 | 11/1977 | Chandrasekaran | 128/260 |
| 4,409,206 | 10/1983 | Stricker | 424/81 |
| 4,588,580 | 5/1986 | Gale et al. | 424/195.1 |
| 4,626,539 | 12/1986 | Aungst | 514/282 |
| 4,685,911 | 8/1987 | Konno et al. | 424/450 |
| 4,859,685 | 8/1989 | Jerussi | 514/329 |
| 4,906,463 | 3/1990 | Cleary et al. | 424/449 |
| 5,213,568 | 5/1993 | Lattin et al. | 604/20 |
| 5,225,198 | 7/1993 | Sharma | 424/443 |

OTHER PUBLICATIONS

Maze, Mervyn, "Clinical Uses of Alpha-2 Agonists", pp. 162, 1–6, 1994.
American Hospital Formulary Service, McEvoy (Ed) pp. 591–594, 1989.
Anesthesiology, 71:178–187 (1989).
Anesthesiology, 70:928–934 (1989).
Anesthesiology, 64:36–42 (1986).
Am. Soc. Anesthesiology, Ann. Rep., Lecture No. 252, 1–6 (1994).
Am. Soc. Anesthesiology, Ann. Rep., Lecture No. 167, 1–6 (Oct., 1994).
PDR 48 Edition 1994, p. 1083.
PDR 44 Edition 1990, pp. 873–874.

*Primary Examiner*—D. Gabrielle Phelan
*Attorney, Agent, or Firm*—Hedman, Gibson & Costigan, P.C.

[57] ABSTRACT

The applicants have discovered that by simultaneously administering particular combinations of drugs at particular dosage levels by means of a transdermal delivery system, anesthesia may be induced in patients requiring such treatment. It has been found that profound sedation or an analgesic effect may be produced by means of a particular combination of pharmacologic agents which are administered simultaneously by transdermal administration. A patch system has been devised which is useful for reversing anesthesia.

12 Claims, 1 Drawing Sheet

METHOD FOR TRANSDERMAL INDUCTION OF ANESTHESIA, ANALGESIA OR SEDATION

BACKGROUND OF THE INVENTION

1. Field of the Invention

This invention relates to a method of inducing general anesthesia, profound sedation and/or analgesia. The invention also provides a method for the reversal of anesthesia, sedation and/or analgesia.

2. Description of the Related Art

In the prior art, general anesthesia has been induced by the administration of well known anesthetic drugs intravenously or by inhalation. These routes of administration provide for the effective and controlled delivery of anesthesia for diverse and varied medical procedures.

Certain lung conditions and vascular conditions particularly in elderly and debilitated patients make it difficult to administer and control inhalation or intravenous anesthesia. In addition, conditions in hyperbaric chambers, submarines, extraterrestrial vehicles, combat zones or at the scene of an accident may render the use of traditional methods of providing anesthesia, sedation or analgesia impractical. For these reasons it is desirable to have available another route of administration by which anesthesia, sedation or analgesia may be provided.

SUMMARY OF THE INVENTION

It has been discovered that by simultaneously administering particular combinations of drugs at particular dosage levels by means of a transdermal delivery system, the surgical stage of anesthesia may be induced in patients requiring such treatment. In addition it has been found that profound sedation or an analgesic effect may be produced by means of a particular combination of pharmacologic agents which are administered simultaneously by transdermal administration.

It has also been discovered that the state of anesthesia may be reversed by the simultaneous transdermal administration of a combination of drugs such as naloxone and an $\alpha_2$-antagonist such as yohimbine, rauwolscine, idazoxan and atepamezole.

In addition the invention also includes the method of reducing the total amount of a general anesthetic agent which is required to provide anesthesia.

Accordingly, it is a primary object of this invention to provide a method for inducing general anesthesia by simultaneously administering a combination of drugs transdermally.

It is a primary object of this invention to provide a method of inducing profound sedation by simultaneously administering a combination of drugs transdermally.

It is also a primary object of this invention to provide a method of providing analgesia by simultaneously administering a combination of drugs transdermally.

It is also a primary object of this invention to provide a simplified method of providing anesthesia, sedation or analgesia that may be administered by paramedics and other emergency personnel who are not physicians.

It is also a primary object of this invention to provide a simplified method of reversing by transdermal patch, anesthesia, sedation or analgesia.

These and other objects of the invention will become apparent from a review of the specification.

DESCRIPTION OF THE PREFERRED EMBODIMENTS

General anesthesia may be induced by simultaneously administering a combination of the following drugs transdermally:

(a) fentanyl or a fentanyl analog;

(b) an $\alpha_2$-adrenergic agonist such as clonidine; guanfacine, guanabenz, dexmedetomine, xylazine, azepezole, B-HT 920, UK-14,404, milvazerol, $\alpha$-methylnorepinephrine and oxymetazoline.

(c) an amnesia inducing drug selected from the group consisting of scopolamine, ketamine and benzodiazepines.

The drug combination for inducing anesthesia may be administered from a special multicompartment transdermal patch or from individual transdermal patches that are sequentially applied.

Patches which supply clonidine and fentanyl are commercially available and are described in the prior art For example U.S. Pat. Nos. 4,906,463; 4,588,580; 4,685,911 and 4,626,539 disclose techniques for making useful transdermal patches which may be used for the practice of the present invention. An amnesia inducing drug which is commercially available as a patch is scopolamine. In addition, Remington's Pharmaceutical Sciences, 1985 Ed., Mack Pub. Co., Easton, Pa. at pp 1567–1572 discloses the procedures which are known to the art for the making and testing of transdermal drug delivery systems. The Physican's Desk Reference, 1990 Ed., pp 873–874, describes the commercial scopolamine transdermal patch which is sold under the SCOP trademark. These publications are incorporated by reference.

Figure 1:
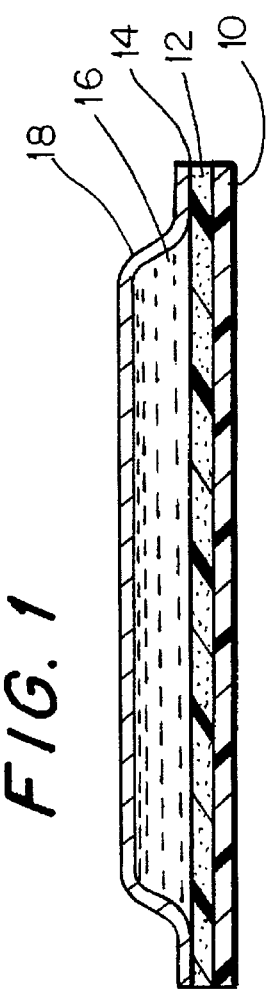
FIG. 1 is a cross-section of a transdermal patch according to the present invention.

A cross-section of a transdermal patch is shown in FIG. 1. A protective peel-away layer 10 may be made of a material such as siliconized polyethylene terephthalate. The layer 12 which is immediately adjacent to the peel-away layer 10 is made of mineral oil, polyisobutylene and 0.15–0.3 mg. of scopolamine.

A microporous membrane of polypropylene 14 is provided to control the rate of delivery of scopolamine from the drug reservoir 16 which contains a solution of polyisobutylene, mineral oil and scopolamine so that about 0.3 mg of scopolamine is delivered over a 20 minute period. Occlusive backing layer 18 provides a solvent impenetrable layer which is shaped to form a compartment which functions as drug reservoir 16.

The amount of scopolamine which is released is proportional to its surface area and the porosity of the membrane. During the manufacturing process, about 0.3–0.7 mg of the scopolamine is placed only in the reservoir but during storage, the scopolamine will equilibrate through the microporous membrane with the adhesive layer. The scopolamine in the adhesive layer should be about 0.15 mg which will provide a loading dose of scopolamine. The initial action of the scopolamine induces a mild tachycardia which will be compensated for by the bradycardia that is induced by fentanyl and clonidine. The area of the patch which delivers scopolamine is about 5 $cm^2$. which is equivalent to about 2 commercially available patches.

Other amnesia inducing drugs include ketamine which has an effective plasma level concentration of 100–150 ng/ml. Benzodiazepines such as midazolam, which has an effective plasma level concentration of 50–150 ng/ml may also be formulated in a transdermal patch as an amnesia inducing drug. Other benzodiazepines include diazepam, oxazepam, lorezepam, prazepam, chlordiazepoxide and alprazolam. The effective plasma level concentrations of the benzodiazepines may be determined from the literature or by means of standard pharmacological tests.

The transdermal patches containing clonidine and fentanyl may be prepared using the same structure and materials that are shown in FIG. 1.

The clonidine transdermal patch will have about 2.5 mg of clonidine in the reservoir portion, a loading dose of clonidine in the adhesive layer of about 0.2 mg of clonidine and a total area of about 10.5 $cm^2$.

The fentanyl transdermal patch will have about 20–100 mg of fentanyl in the reservoir portion, a loading dose of fentanyl in the adhesive layer of about 400–500 μg of fentanyl and a total area of about 80–200 $cm^2$. The fentanyl analogs which may be used in the present invention include sufentanil, carfentanil, lofentanil, remifentanil and alfentanil.

Figure 2:
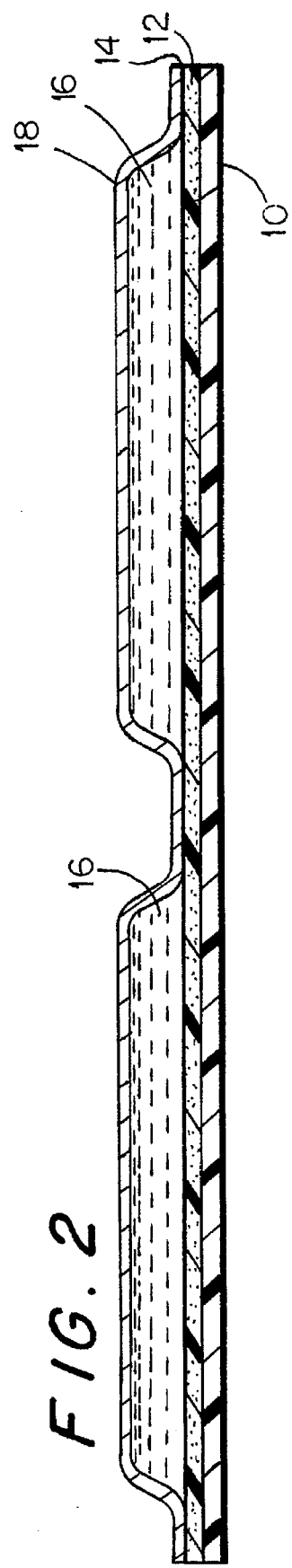
FIG. 2 is a cross-section of a multicompartment transdermal patch according to the present invention.

The multicompartment patch of the invention is shown in FIG. 2 wherein two adjacent compartments are provided for clonidine and fentanyl. This patch may be used in conjunction with a separate patch containing scopolamine which is placed on the skin about 20 minutes prior to the application of the multicompartment patch or separately to provide an analgesic effect.

Profound sedation may be induced by the use of the novel patch of FIG. 2 which provides simultaneous administration of clonidine and fentanyl.

The drug combination for inducing sedation may be administered from a special multicompartment transdermal patch or from individual transdermal patches that are sequentially applied.

The combination of naloxone and an $\alpha_2$-antagonist may be formulated as a combined system in a single patch or multiple independent patches may be employed. The amount of the naloxone administered 2 to 5 mg and the amount of the $\alpha_2$-antagonist will be from 5 to 10 mg.

The patch system of the invention may also be utilized in combination with the electrotransport delivery system disclosed in U.S. Pat. No. 5,213,568, which is incorporated by reference.

The following Examples are to further illustrate the invention and they are not intended to be construed as a limitation of the scope of the invention. Patches are commercially available for fentanyl, clonidine and scopolamine or they may be made using procedures that are described in the literature using routine experimentation to determine the optimum combination of materials and drug concentrations to achieve a desired therapeutic result.

EXAMPLE 1

A mixture of 3.5% by weight of fentanyl base and 96.5% by weight of polyisobutylene are dissolved in n-hexane to provide a 33% soilds solution. A drug reservoir is prepared by casting the fentanyl-polyisobutylene solution onto a flurocarbon coated polyethylene terephthalate film using a cast blade. The n-hexane (solvent) is evaporated to yield a drug reservoir film which is laminated onto a 12.5 micron thick structural polyethylene terephthalate film.

A pressure-sensitive adhesive consisting of 1.5% by weight fentanyl base, 3.5% by weight propylene glycol monolaurate, 2.5% by weight silicone oil (100 centistoke, Dow Corning Medical Fluid) and 92.5% by weight of amine resistant polydimethylsiloxane (Dow Corning X7-2900) is dissolved with trichlorotrifluoroethane to provide a 50% by weight solution. The adhesive is cast using a 150 micron gap Gardner wet film applicator onto a fluorocarbon-coated polyethylene terephthalate film and the solvent is evaporated to provide a 75 micron thick contact adhesive layer. The adhesive is laminated onto a second moisture permeable structural support film consisting of 12.5 micron thick polyethylene terephthalate film (Medifilm 428 or 827) so that the polyethylene terephthalate film acts as a release strip to provide a structural support/adhesive/release/strip laminate composite.

The fluorocarbon-coated polyethylene terephthalate release strip is removed and the drug reservoir surface is laminated to the 12.5 micron thick polyethylene terephthalate film to provide the final laminated composite with the polyethylene terephthalate film serving as a peelable release strip for the final laminate. The laminate is allowed to equilibrate for a period of one week prior to use and cut into transdermal patches having an area of 100 $cm^2$.

EXAMPLE 2

Using the procedure of Example 1, a transdermal patch containing clonidine is prepared which has sufficient clonidine to provide a plasma level of about 5 ng/ml.

EXAMPLE 3

The anesthesia inducing method of the invention may be carried in a mammal such as a rat using the following procedure. A commercial depilatory product is applied to the rat's fur and a 60–80 $cm^2$ area of nude skin is exposed. The first transdermal patch containing 0.5 mg. of scopolamine (the commercial product TranScop is used) is applied to the nude skin. After 5 minutes, a transdermal patch containing 10 mg. of fentanyl (the commercial product Duragesic is used) and a transdermal patch containing 7.5 mg. of clonidine (the commercial product Catapres-TTS-rate of delivery =0.3 mg./day) is applied to the nude skin of the rat. After 10 to 15 minutes, the rat is observed to be in a state of anesthesia, as characterized by a reduction in blood pressure, loss of corneal reflex, a decrease in the rate of respiration (shallow and irregular) which would permit the carrying out of any necessary surgical procedure. The animals are unresponsive to thermal stimuli, and extreme pressure applied to their tail (no tail-flick response), measures which indicate that the animals are feeling no pain and are properly sedated which is important in establishing and maintaining anesthesia.

After the surgical procedure is completed, the patches are removed and a new series of patches are applied to reverse the effects of the anesthetic patch system. The reversing patch contains 2 mg of naloxone which reverses the action of fentanyl and 5 mg of yohimbine which reverses the effect of clonidine. After the application of the reversal patch system, the rat is observed to return to the conscious state in a period of about 10 to 15 minutes.

EXAMPLE 4

One hour prior to the scheduled induction of general anesthesia, a 0.3 mg. clonidine patch (Catapres-TTS) and two 100 mcg/hour fentanyl (Duragesic) patches are applied to the chest wall of a patient. The patient will become sedated in a slow gradual manner and a marked reduction in anxiety is noted. When the patient is subsequently anesthetized with sodium pentothal, less than one-half of the usual dose of sodium pentothal is required and the amount of isoflurane which is required to prevent movement is reduced by 40 to 50%.

EXAMPLE 5

Four patients undergoing elective laminectomy for a herniated vertebral disk, were anesthetized by first applying one 0.3 mg clonidine patch (Catapres-TTS) and two 100 mcg/hour fentanyl patches (Duragesic) to the chest wall of each patient. During maintenance of anesthesia, the amount of isoflurane needed to prevent movement was decreased by about 50% (approximately 0.5 MAC) The operation required about 1.5 hours and the patches were removed at the end of the operation.

Postoperatively, the patients were found to have an Aldrete score (a scale of 5 measures of recovery from general anesthesia, namely consciousness, respiration, activity, color, blood pressure/circulation) of between 9 and 10 upon admission to the recovery room (with 10 being a score which connotes readiness for discharge from the recovery room). Normally these patients have an Aldrete score of 6–7. It was also noted that the amount of pain medication (morphine) required to keep the patients pain free post-operatively was significantly reduced compared to patients that did not receive the patches. The verbal analogue pain scores (an inverse measure of analgesia) were found to be between 0–2 for the first 6 hours after surgery. Normally these scores are in the range of 3–6.

EXAMPLE 6

A two-compartment patch modeled after FIG. 1 which contains in one compartment, 2.0 mg naloxone dissolved in mineral oil and in another compartment 5.0 mg of yohimbine dissolved in mineral oil is immediately applied to the chest wall after removal of a patch system containing fentanyl and clonidine. The patient regains consciousness in about 10 to 15 minutes.

We claim:

1. A method of inducing surgical anesthesia in a mammal, said method comprising (a) transdermally administering via a transdermal patch an amount of an amnesia producing drug selected from the group consisting of scopolamine, ketamine and benzodiazepines which is effective to produce amnesia, and (b) after an amnesic state is produced by said amnesia producing drug, transdermally administering amounts of clonidine and fentanyl which are sufficient to produce surgical anesthesia.

2. A method as defined in claim 1 wherein the amnesia inducing drug is scopolamine.

3. A method of inducing sedation in a mammal, said method comprising (a) transdermally administering via a transdermal patch an amount of an amnesia producing drug which is effective to produce amnesia, and (b) after an amnesic state is produced by said amnesia producing drug, transdermally administering amounts of clonidine and fentanyl or a fentanyl analog which are sufficient to produce sedation.

4. A method as defined in claim 3 wherein the amnesia producing drug is selected from the group consisting of scopolamine, ketamine and benzodiazepines.

5. A method as defined in claim 4 wherein the amnesia inducing drug is scopolamine.

6. A method of providing anesthesia to a mammal, said method comprising transdermally administering via a transdermal patch amounts of clonidine and fentanyl or a fentanyl analog which are sufficient to produce surgical anesthesia.

7. A method of reversing surgical anesthesia in a mammal, said method comprising (a) transdermally administering via a transdermal patch an amount of naloxone, and (b) an amount of an $\alpha_2$-antagonist selected from the group consisting of yohimbine, rauwolscine, idazoxan and atepamezole which is sufficient to reverse surgical anesthesia.

8. A method of inducing surgical anesthesia in a mammal, said method comprising (a) transdermally administering via a transdermal patch an amount of an amnesia producing drug selected from the group consisting of scopolamine, ketamine and benzodiazepines which is effective to produce amnesia, and (b) after an amnesic state is produced by said amnesia producing drug, transdermally administering via a transdermal patch amounts of clonidine and fentanyl or a fentanyl analog which are sufficient to produce surgical anesthesia.

9. A method of inducing anesthesia in a mammal, said method consisting essentially of (a) transdermally administering via a transdermal patch amounts of clonidine and fentanyl analog which are sufficient to produce anesthesia.

10. A method as defined in claim 8 wherein the fentanyl analog is selected from the group consisting of sufetanil, carfentanil, lofentanil, remifentanil and alfentanil.

11. A method of reversing surgical anesthesia in a mammal, said method comprising (a) transdermally administering via a transdermal patch an amount of naloxone, and (b) an amount of yohimbine which is sufficient to reverse surgical anesthesia.

12. A method of inducing surgical anesthesia in a mammal, said method comprising (a) transdermally administering via a transdermal patch an amount of an amnesia producing drug selected from the group consisting of scopolamine, ketamine and benzodiazepines which is effective to produce amnesia, and (b) after an amnesic state is produced by said amnesia producing drug, transdermally administering via a transdermal patch amounts of clonidine and fentanyl which are sufficient to produce surgical anesthesia.

* * * * *